United States Patent [19]

Maruno et al.

[11] Patent Number: 5,204,457
[45] Date of Patent: Apr. 20, 1993

[54] ORGANIC MAGNETIC COMPLEX

[75] Inventors: Shigeo Maruno, 134, Sakuragaoka 4-chome, Kani-shi, Gifu 509-02; Masakatsu Hasegawa, Nagoya, both of Japan

[73] Assignees: Meito Sangyo Kabushiki Kaisha, Nagoya; Shigeo Maruno, Kani, both of Japan

[21] Appl. No.: 720,504

[22] PCT Filed: Oct. 19, 1990

[86] PCT No.: PCT/JP90/01346

§ 371 Date: Jun. 20, 1991

§ 102(e) Date: Jun. 20, 1991

[87] PCT Pub. No.: WO91/05807

PCT Pub. Date: May 2, 1991

[30] Foreign Application Priority Data

Oct. 20, 1989 [JP] Japan .................. 1-271784

[51] Int. Cl.$^5$ .................................... C08B 11/12
[52] U.S. Cl. .................... 536/101; 252/62.57; 252/62.58; 252/62.64; 252/62.56; 252/62.53
[58] Field of Search .............. 252/62.57, 62.58, 62.63, 252/62.64, 62.56, 62.53; 536/101

[56] References Cited

U.S. PATENT DOCUMENTS 4,101,435 7/1978 Hasegawa et al. ............... 252/62.53
4,452,773 6/1984 Molday ........................... 436/526

FOREIGN PATENT DOCUMENTS 59-93097 5/1984 Japan .
59-122501 7/1984 Japan .

OTHER PUBLICATIONS

CA 84,831b Sep. 5, 1988, Wooding et al. in *IEEE Trans. Magn.* 1988, 24(2,Pt. 2), 1650-2.

*Primary Examiner*—Nathan M. Nutter
*Assistant Examiner*—Jeffrey C. Mullis
*Attorney, Agent, or Firm*—Wenderoth, Lind & Ponack

[57] ABSTRACT

A complex of a carboxyalkyl ether of a polysaccharide with a magnetic metal oxide. This complex is extremely excellent in stability in preservation in the form of aqueous sol and has only a low toxicity, and thus is useful, for example, for medical use as a nuclear magnetic imaging molding agent or the like.

20 Claims, 5 Drawing Sheets

FIG. I

ORGANIC MAGNETIC COMPLEX

TECHNICAL FIELD

This invention relates to a complex of a carboxyalkyl ether of a polysaccharide with a magnetic metal oxide and a process for preparing thereof.

BACKGROUND ART

Usual magnetic fluids are prepared with the addition of a surfactant such as a oleate salt or a dodecylamine in order to make the superfine particles of a magnetic metal oxide or magnetic metal stably existing in a liquid such as water or an oil. Since usual magnetic fluids are poor in chemical stability and have high toxicity, trials to apply them to medical treatment have scarcely been made.

In order to obviate these drawbacks, complexes of dextran with a magnetic iron oxide have been proposed, and for example, Japanese Patent Publication No. 13521/1984 (U.S. Pat. No. 4,101,435) discloses complexes of dextran or a modified dextran obtained by treating dextran with sodium hydroxide and a magnetic iron oxide having a size of 3 to 20 nm. Further, U.S. Pat. No. 4,452,773 discloses magnetic iron-dextran microspheres of a molecular complex structure such that magnetic iron oxide particles having a colloidal size was coated with dextran molecules. Although these complexes are useful in the form of aqueous sol, they still have problems to be improved particularly for use in medical treatment.

As a result of intensive studies, the present inventors found that complexes of a carboxyalkyl ether of a polysaccharide with a magnetic metal oxide have improved properties in several points, and came to complete the invention.

DISCLOSURE OF INVENTION

Thus, according to the invention, is provided a complex of a carboxyalkyl ether of a polysaccharide with a magnetic metal oxide.

Complexes of the invention are extremely excellent in stability in preservation in the form of aqueous sol and have only low toxicity, and thus are useful for medical treatment, for example, as a nuclear magnetic resonance imaging (hereinafter abbreviated as MRI) contrast medium or a drug-administering carrier or the like.

As for carboxyalkyl ethers of a polysaccharide as one component constituting the complexes of the invention, at least part of them, are known for example, refer to U.S. Pat. Nos. 2,746,906 and 2,876,165, Kogyo Kagakukaishi, 68, 1590 (1965), and such an ether can readily be prepared by adding an alkali to an aqueous solution or suspension of a polysaccharide and then adding a monohaloalkylcarboxylic acid, particularly a monochloroalkylcarboxylic acid to start reaction. A polysaccharide carboxyalkyl ether having a desired limiting viscosity can be obtained by using the polysaccharide having a corresponding intrinsic viscosity as a starting material or by first preparing the polysaccharide carboxyalkyl ether having a high viscosity and then lowering the viscosity. Polysaccharides usable as a starting raw material include neutral polysaccharides and basic polysaccharides, and examples of neutral polysaccharides are glucose polymers such as dextran, starch, glycogen, cellulose, pullulan, curdlan, schizophyllan, lentinan and pestalotian; fructose polymers such as inulin and levan; mannose polymers such as mannan; galactose polymers such as agapose and galactan; xylose polymers such as xylan; L-arabinose polymers such as arabinan; etc, and examples of basic polysaccharides are glucosamine polymers such as chitin.

In the invention, neutral polysaccharides are preferred among them, and particularly preferred are dextran, starch, cellulose and pullulan.

On the other hand, as haloalkylcarboxylic acids usable for the carboxyalkyl etherification of the polysaccharide, halo-lower alkylcarboxylic acids are particularly mentioned, and examples thereof are monochloroacetic acid, monobromoacetic acid, 3-chloropropionic acid, 3-bromopropionic acid, 4-chloro-n-butyric acid, 4-bromo-n-butylic acid, 2-chloropropionic acid, 3-chloro-n-butyric acid, etc.

Preferred carboxyalkyl ethers of the polysaccharide in the invention are at least one selected from carboxymethyl ethers, carboxyethyl ethers and carboxypropyl ethers.

When reacted with a magnetic metal oxide, the polysaccharide carboxyalkyl ether may be either in the state of free carboxyl groups or in the form of a salt, and examples of the salt are alkali metal salts, amine salts, ammonium salts, etc., specifically sodium salts. When used in either form, the polysaccharide carboxyalkyl ether is desirably water soluble and its intrinsic viscosity can be generally in the range of about 0.02 to about 0.5 dl/g, preferably about 0.05 to about 0.3 dl/g.

Further, the substitution degree of the polysaccharide carboxyalkyl ether is generally in the range of about 0.05 to about 1.0 mol/MSU, preferably about 0.1 to 0.5 mol/MSU. "MSU" in this description means a monosaccharide unit. Further, "intrinsic viscosity" and "substitution degree" of the polysaccharide carboxyalkyl ether are values obtained as a result of the following measurements.

The intrinsic viscosity $[\eta]$ of the polysaccharide carboxyalkyl ether is measured at 25° C. according to the method disclosed in Viscosity Measurement Method, Item 30, General Tests, The Pharmacopoeia of Japan (Eleventh Edition, 1986). The solvent to be used therein is a 1M aqueous solution of a chloride of the same cation as the counter ion (carboxylate salt ion) possessed by the polysaccharide carboxyalkyl ether. However, when the counter ion of the polysaccharide carboxyalkyl ether is a hydrogen ion (i.e., free carboxyl group), intrinsic viscosity is measured using the polysaccharide carboxyalkyl ether sodium salt obtained by neutralizing this polysaccharide carboxyalkyl ether with an aqueous sodium hydroxide solution.

On the other hand, the substitution degree of the polysaccharide carboxyalkyl ether is measured separately in accordance with the following occasions.

(1) In case where the counter ion of the carboxyl groups of the polysaccharide carboxyalkyl ether is a metal ion such as an alkali metal ion A polysaccharide carboxyalkyl ether is dissolved in water, and the solution is appropriately diluted to give a measurement sample solution. The sample solution and a standard sample (known concentration) of a metal ion as the counter ion are measured for metal content according to the method disclosed in Atomic Absorption Spectrophotometry, Item 17, General Tests, The Pharmacopoeia of Japan (Eleventh Edition, 1986), and the substitution degree of the polysaccharide carboxyalkyl ether is calculated as mole number per monosaccharide unit.

(2) In case where the counter ion of the carboxyl groups of the polysaccharide carboxyalkyl ether is a hydrogen ion A polysaccharide carboxyalkyl ether is dissolved in water, the solution is neutralization titrated with an aqueous sodium hydroxide solution, and the substitution degree of the polysaccharide carboxyalkyl ether is calculated from the amount of the consumed sodium hydroxide as mole number per monosaccharide unit.

(3) In case where the counter ion of the carboxyl groups of the polysaccharide carboxyalkyl ether is ammonia or an amine According to the method disclosed in Nitrogen Determination, Item 26, General Tests, The Pharmacopoeia of Japan (Eleventh Edition, 1986), the nitrogen content of the polysaccharide carboxyalkyl ether is measured, and the substitution degree of the polysaccharide carboxyalkyl ether is calculated as mole number per monosaccharide unit.

In the invention, carboxyalkyl ethers of a modified polysaccharide obtained by reduction with an appropriate reducing agent are particularly preferred because of their low coloring. Reduction methods for such polysaccharides include several methods, and for example, U.S. Pat. No. 2,807,610 discloses as reduction methods for dextran a method using sodium amalgam, a method using hydrogen gas in the presence of palladium carbon, a catalyst and a method using sodium borohydride (NaBH$_4$). The method using sodium borohydride is particularly preferred, and according to the method, powders of a reduced polysaccharide can be obtained by adding sodium borohydride in an amount of 5 times or more the theoretical amount to a 5 to 20% aqueous solution of a polysaccharide with stirring, stirring the mixture at room temperature for further 5 hours, adding acetic acid to adjust the pH to about 6, passing the mixture through the columns of a cation exchange resin (for example, Amberlite ® IR-120) and then an anion exchange resin (for example, Amberlite ® IR-45), and drying the eluate either as such or after concentration under reduced pressure by a method such as a freeze drying method or a spray drying method.

The magnetic metal oxide, the other component of the complex of the invention is a ferromagnetic substance, and the magnitude of coercive force does not particularly come into question so long as the degree of magnetization is larger than a certain degree.

As such magnetic metal oxides, there can be exemplified those represented by the following formula

$$(M^{II}O)_l \cdot M_2^{III}O_3 \qquad (I)$$

wherein $M^{II}$ represents a divalent metal atom, $M^{III}$ represents a trivalent metal atom and l is a real number in the range of $0 \leq l \leq 1$. In the above formula (I), examples of the divalent metal atom $M^{II}$ are magnesium, calcium, manganese, iron, nickel, cobalt, copper, zinc, strontium, barium, etc., and they can be used alone or in a combination of two or more. Further, examples of trivalent metal atom $M^{III}$ are aluminum, iron, yttrium, neodymium, samarium, europium, gadolinium, etc., and they can be used alone or in a combination of two or more.

Preferred are magnetic metal oxides of the formula (I) wherein $M^{III}$ is trivalent iron, namely ferrites represented by the following formula

$$(M^{II}O)_m \cdot Fe_2O_3 \qquad (II)$$

wherein $M^{II}$ is as defined above and m is a real number in the range of $0 \leq m \leq 1$. As $M^{II}$ metals, there can be mentioned the same metals as exemplified in the formula (I). Particularly, there can be mentioned as preferred magnetic metal oxides in the invention the magnetic metal oxides of the formula (II) wherein $M^{II}$ is divalent iron, namely magnetic iron oxides represented by the following formula

$$(FeO)_n \cdot Fe_2O_3 \qquad (III)$$

wherein n is a real number in the range of $0 \leq n \leq 1$. In the above (III), the compound in case of n=0 is γ-iron oxide (γ-Fe$_2$O$_3$) and the compound in case of n=1 is magnetite (Fe$_3$O$_4$).

Further, the magnetic metal oxides in the invention can also be magnetic metal oxides represented by the formula

$$M^{II}M^{IV}O_3 \qquad (IV)$$

and

$$M^{IV}O_2 \qquad (V)$$

wherein $M^{II}$ represents a divalent metal atom and $M^{IV}$ represents a tetravalent metal atom. In the above, as the divalent metal atom $M^{II}$ there can be exemplified those described above, and examples of the tetravalent metal atom are vanadium, chromium, manganese, etc.

Specific examples of magnetic metal oxides represented by the formula (IV) or (V) are, for example, NiMnO$_3$, CoMnO$_3$, CrO$_2$, etc. Magnetic metal oxides in the invention include magnetic metal oxides having crystallization water, too.

Magnetic metal oxides stated above can be ferromagnetic substances, and, in general, it is desirable for the oxides to have a magnetization in the range of about 1 to about 150 emu, preferably about 10 to about 150 emu, more preferably about 30 to about 150 emu per 1 g of the metal at 20° C. and at a magnetic filed of 1 tesla (10,000 oersteds).

The magnetic metal oxide is reacted, usually in the form of fine particles, with the polysaccharide carboxyalkyl ether. Generally, the magnetization of magnetic substance particles lowers in proportion to the decrease of their particle size, and the trend becomes stronger particularly when the particle size becomes 10 nm or less. Further, the coercive force of the magnetic metal oxide lowers in proportion to the decrease of its particle size when the particle size is 100 nm or less, and when the particle is 15 nm or less, the magnetic metal oxide substantially becomes superparamagnetic.

When the magnetic metal oxide in the invention is used in the form of sol, it is convenient that it has a particle size in the range of generally about 2 to about 100 nm, preferably about 3 to about 30 nm, and more preferably about 5 to about 15 nm. Further, when the magnetic metal oxide is used in the form of suspension, it is convenient that it has a particle size in the range of generally about 0.1 to about 5 μm.

Magnetic metal oxide particles exhibit a diffraction pattern corresponding to a specific magnetic substance in X-ray diffraction. Therefore, from the results of the metal analysis and X-ray diffraction of magnetic substance particles, the kind of the magnetic substance can be identified. Further, it is surmised that the surface of the magnetic particles has a structure different from the crystal structure of the inside. However, since even in this case the X-ray diffraction pattern exhibits a specific pattern in accordance with the crystal structure of the inside, the kind of the ferromagnetic substance can similarly be identified even in this case from the results of metal analysis and X-ray diffraction and the like. The indications of the general formulae (I) to (V) in the present description mean the compositions of magnetic substance particles obtained by these measurements.

Processes for preparing complexes of the invention from the foregoing polysaccharide carboxyalkyl ethers and magnetic metal oxides can roughly be classified into the following two processes. Namely, the first process is a process which comprises first preparing an aqueous sol or suspension containing magnetic metal oxide particles which will be the core of the complex, and subjecting it to reaction with a carboxyalkyl ether of a polysaccharide. The second process is a process which comprises mixing a divalent metal salt, a trivalent metal salt and a base with stirring in an aqueous system in the presence of a polysaccharide carboxyalkyl ether to progress reaction.

In the first process, first an aqueous sol or suspension containing magnetic particles (hereinafter referred to as magnetic raw material liquid) is prepared, and the liquid is reacted with the etherified substance to form a complex, and in this process the particle size and magnetism of the magnetic particles in the magnetic raw material are substantially the same with those of the magnetic particles contained in the obtained complex Namely, many of the physical properties of the complex are greatly influenced by the physical properties of the magnetic particles contained in the magnetic raw material liquid. Therefore, it is necessary to previously prepare the magnetic raw material liquid containing the magnetic particles having physical properties in accordance with the object. For example, when it is desired to use the complex in the form of sol, it is desirable for the diameter of the magnetic particles contained in the magnetic raw material liquid to be in the range of about 2 to about 100 nm, preferably about 3 to about 30 nm, more preferably about 5 to about 15 nm.

The preparation of a magnetic raw material liquid containing magnetic particles can be made by a method known per se. For example, an alkali coprecipitation method can be employed, and specifically, a magnetic iron oxide aqueous sol can be obtained, for example, by mixing an aqueous solution containing a ferrous salt of a mineral acid and a ferric salt of a mineral acid in a weight ratio of about 1:3 to about 1:0.5 with a base such as NaOH, KOH or NH$_4$OH so that the pH becomes 7 to 12, if necessary ageing the mixture with heating, separating the formed magnetic iron oxide particles, washing them with water, redispersing them in water, and adding a mineral acid such as hydrochloric acid to make the pH 1 to 3. This aqueous sol can, if necessary, be purified and/or concentrated by dialysis, ultrafiltration, centrifugation, etc. The magnetic iron oxide particles obtained by this method can have a diameter usually in the range of about 5 to about 50 nm. A ferrite aqueous sol can similarly be obtained by using a salt of a divalent metal other than iron in place of part of or all the ferrous salt in the above method. The ferrite particles contained in the sol have a diameter usually in the range of about 5 to about 50 nm. Examples of usable divalent metal salts are mineral acid salts of magnesium, zinc, cobalt, manganese, nickel, copper, barium, strontium, etc., and these can be used alone or at the same time in plural. Further, magnetic raw material liquid can also be prepared by the method disclosed in Japanese Patent Publication No. 24663/1967 (U.S. Pat. No. 3,480,555). For example, an aqueous sol of a magnetic iron oxide can be obtained by adding an aqueous solution containing a ferrous salt and a ferric salt in the weight ratio of about 1:2 to a stirred strongly basic ion exchange regin slurry while the mixture is maintained to pH 8 to 9, adding a mineral acid such as hydrochloric acid until the pH becomes 1 to 3, filtering the resin, and, if necessary, purifying and/or concentrating the filtrate by dialysis, ultrafiltration, etc. The contained magnetic iron oxide particles have a diameter usually in the range of about 5 to about 15 nm.

Further, as a process for preparing a magnetic raw material liquid containing magnetic particles having a relatively large diameter, there can be mentioned a process which comprises adding a base such as NaOH, KOH NH$_4$OH to a stirred aqueous solution of a ferrous salt until the pH of the mixture becomes 7 to 12, blowing air or O$_2$ gas through it with heating for about 2 to about 20 hours, separating and water washing the formed magnetic iron oxide particles, and forming an aqueous suspension of the magnetic iron oxide. By this method, there can be formed magnetic iron oxide particles having a diameter usually in the range of about 0.1 to about 5 μm.

A complex can be formed by mixing and reacting the thus obtained magnetic raw material liquid with an aqueous solution of a polysaccharide carboxyalkyl ether. More specifically, the polysaccharide carboxyalkyl ether is reacted with the magnetic particles contained in the magnetic raw material liquid, for example in the rate of usually 0.1 to 10 weight parts, preferably 0.2 to 5 weight parts of the former per 1 weight part (in terms of metal) of the latter particles. In this connection, it is convenient in general that when the magnetic particles having a small diameter are used, the addition amount of the etherified compound is increased, while when the magnetic particles having a large diameter is used, the addition amount of the etherified compound is reduced. Although the concentration of the magnetic particles in the reaction mixture is not particularly limited, it can be in the range of usually 0.1 to 10 W/V %, preferably 1 to 5 W/V % in terms of the metal. Although the reaction can generally be carried out at a temperature i the range of room temperature to 120° C. for 10 minutes to 10 hours, for convenience it is sufficient to reflux the reaction mixture with heating for about 1 hour. After cooling, it is possible, if necessary, to carry out purification and/or concentration adjustment. For example, it is possible to obtain an aqueous sol or aqueous suspension of the complex having the desired purity and concentration by repeating the operation to separate the unreacted etherified substance and low molecular compounds from the formed complex by ultrafiltration; and it is further possible to obtain an aqueous sol of the complex having the desired purity and concentration by adding to the formed reaction mixture a poor solvent to the complex such as methanol, ethanol or acetone to precipitate and deposit the complex preferentially, separating the precipitate, redissolving the precipitate in water, dializing the solution again running water, and then, if necessary, concentrating the solution under reduced pressure; and further, in case of the reaction mixture containing the magnetic particles having a large particle size, it is also possible to obtain an aqueous suspension of the complex having the desired purity and concentration by repeating as such centrifugation and water washing. In the above, if desired, it is also possible to add the steps for pH adjustment, centrifugation and/or filtration during and/or after the above steps. It is also possible to obtain the complex of the invention in the form of powder by drying the thus obtained aqueous liquid of the complex of the invention by a method known per se, for example preferably by freeze drying.

The second process for preparing the complex of the invention is a process for obtaining the complex of the invention in one step by mixing and reacting a mixed metal salt solution of a mineral acid salt of a divalent metal and a mineral acid salt of a trivalent metal with a solution of a base in an aqueous system in the presence of a polysaccharide carboxyalkyl ether. This second process can further be classified, by addition order, into (A) a process which comprises adding the mixed metal salt solution to an aqueous solution of the ether, and then adding an aqueous base solution to progress reaction; (B) a process which comprises adding an aqueous base solution to an aqueous solution of the ether, and then adding the mixed metal salt solution to progress reaction; (C) a process which comprises adding to an aqueous base solution a mixed solution of a aqueous solution of the ether and the mixed metal salt solution; (D) a process which comprises adding to the mixed metal salt solution a mixed solution of an aqueous solution of the ether and an aqueous base solution; etc. These (A), (B), (C) and (D) processes are different with one another only in addition order, and not essentially different in other reaction conditions.

In the preparation of the above aqueous mixed metal salt solution, when for example, the divalent metal salt is a ferrous salt and the trivalent metal salt is a ferric salt, the ferrous salt and the ferric salt are dissolved in an aqueous medium in a mole ratio of the former to the latter of about 1:4 to about 3:1, preferably about 1:3 to about 1:1. In this case, it is possible to replace part of, for example about a half amount of the ferrous salt by another divalent metal salt, for example a salt of at least one metal of magnesium, zinc, cobalt, manganese, nickel, copper, barium, strontium and the like. Although the concentration of the aqueous mixed metal salt solution can be varied over a wide range, it is suitable that the concentration is in the range of usually about 0.1 to about 3M, preferably about 0.5 to about 2M.

Examples of the metal salts are salts with mineral acids such as hydrochloric acid, sulfuric acid and nitric acid, and as the base there can for example be used at least one selected from alkali metal hydroxides such as NaOH and KOH; ammonia; and amines such as triethylamine and triethylamine. Although the concentration of the aqueous base solution can be varied over a wide range, it is appropriate that the concentration is in the range of usually about 0.1 to about 10N, preferably about 1 to about 5N. The amount of the base to be used is an amount such that the pH of the reaction solution after the addition becomes almost neutral to about 12, namely an amount that the ratio of the metal salt to the base becomes about 1:1 to about 1:2 (normal ratio).

On the other hand, the amount of the polysaccharide carboxyalkyl ether to be used can be about 1 to about 15 times, preferably about 3 to about 10 times by weight that of the metal in the metal salt to be used. Further, although the concentration of the aqueous polysaccharide carboxyalkyl ether solution is not strictly limited, it is suitably in the range of usually about 1 to about 30 W/V %, preferably about 5 to about 20 W/V %. The addition and mixing of each aqueous solution can be made with stirring at room temperature to about 100° C. with heating, and if necessary after the pH is adjusted with a base or an acid, reaction can be carried out at a temperature of about 30° to about 120° C. for about 10 minutes to about 5 hours, usually by reflux with heating for about 1 hour. Although the above mixing and reaction can usually be carried out under the air atmosphere, they can also be carried out, if desired, under an atmosphere of $O_2$ gas, an inert gas such as $N_2$ or Ar gas or a reducing gas such as $H_2$ gas. The thus obtained reaction solution can be purified in the same manner as in the above first process, and, if desired, can be subjected to pH adjustment, concentration, filtration and further drying. The particle size of the magnetic metal oxide in the obtained complex is usually in the range of about 2 to about 50 nm.

Although the ratio of the polysaccharide carboxyalkyl ether to the magnetic metal oxide in the complex of the invention depends on the diameter of the magnetic metal oxide particles, the molecular weight of the polysaccharide carboxyalkyl ether, etc. and varies in a wide range, the complex can generally contain the polysaccharide carboxyalkyl ether in an amount of about 0.05 to about 10 weight parts, preferably about 0.2 to about 5 weight parts per 1 weight part of the metal in the magnetic metal oxide. More specifically for example, when the magnetic metal oxide is magnetic particles 5 having a diameter of 8 nm, the complex can contain the polysaccharide carboxyalkyl ether in an amount of about 0.5 to about 3 weight parts per 1 part of the metal in the magnetic particles.

The metal content of the complex in the present description (this metal is derived from the magnetic metal oxide as a raw material) is a value measured by the atomic absorption spectrophotometry referred to the above. Namely, hydrochloric acid is added to the complex in the presence of a small amount of water, the contained 5 metal(s) is(are) completely decomposed to chloride(s), the reaction mixture is properly diluted, and the dilution is compared with standard solutions of the respective metals to determine the metal content.

Further, the polysaccharide carboxyalkyl ether content in the complex is a value measured by the sulfuric acid-anthrone method according to Analytical Chem., 25, 1656 (1953). Namely, the sulfuric acid-anthrone reagent is added to a proper dilution of the hydrochloric acid-decomposed solution used for the measurement of metal content to develop color, and the absorbance of the mixture is measured. At the same time, color is likewise developed using as a standard substance the polysaccharide carboxyalkyl ether used in the preparation of the complex, absorbance is measured, and the polysaccharide carboxyalkyl ether content is determined from the ratio of both absorbances.

The diameter of magnetic metal oxide particles to be used in the preparation of the complexes of the invention is either observed with a tramsmission electron microscope only when the diameter is 0.1 $\mu$m or more and determined as an average value, or measured by the X-ray diffraction method when the diameter is 0.1 $\mu$m or less.

Since when the complex powder of the invention obtained freeze drying is subjected to X-ray diffraction using a powder X-ray diffractometer (target: Co, wavelength: 1.790 Å), several diffraction peaks can be observed corresponding to a specific compound, it is seen that the magnetic metal oxide (magnetic particles) contained in the complex exists in a crystalline form. The resulting diffraction peak becomes broader, namely smaller in proportion as the diameter of the magnetic particles contained in the complex decreases. Thus, in case where the particle size of the magnetic metal oxide contained in the complex is 0.1 μm or less, the particle size can be measured by X-ray diffraction. Namely, the particle size (diameter) can be calculated using the following Scherrer equation in respect of the strongest peak in X-ray diffraction.

$$D = k\lambda/\beta \cdot \cos\theta,$$

$$\beta = \sqrt{B^2 - b^2}$$

wherein
- D: particle size (Å)
- k: constant, 0.9
- λ: X-ray wavelength (1.790 Å)
- θ: Bragg angle (degree)
- B: Half-width of the sample (radian)
- b: Half-width of the standard sample (radian)

In the above, the standard sample to be used is the same substance having a particle size of 1 μm or more. The thus obtained value relatively accords with the value obtained form a transmission electron microscope.

Further, the diameter of the complex itself of the invention is the value measured by a light scattering method [for example, refer to Polymer J., 13, 1037-1043 (1981)], and the complex of the invention can have a diameter in the range of generally about 10 to about 500 nm, preferably about 20 to about 200 nm.

The complex of the invention is not a mere mixture, but a compound of magnetic metal oxide particles and a polysaccharide carboxyalkyl ether. This can be understood from the facts, for example, that when an aqueous sol of the complex of the invention is fractionated using a gel column, an elution peak is observed at a high molecular side higher than the elution position of the polysaccharide carboxyalkyl ether and both metals used for the preparation of the saccharide and the complex are detected by the analysis of the peak, and that when in the preparation step for the complex, purification is carried out using an ultrafiltration film having a pore size capable of passing particles smaller than the polysaccharide carboxyalkyl ether molecule, the ratio of the saccharide to the metal in the remaining aqueous sol gradually converge on a certain value.

Further when the complex of the invention and a more mixture of the magnetic particles with the polysaccharide carboxyalkyl ether are each measured by the diffuse reflectance method, a kind of infrared spectroscopic analysis, difference is recognized between the peak positions near 1600 cm$^{-1}$. Infrared spectroscopic measurement can be carried out under the following conditions using FT-IR (model: JIR-100) produced by JEOL Ltd. and a detector: MCT (mercury-cadmium-tellurium alloy).

Sample form: powder obtained by sufficient grinding in a mortar
  Control: KBr
  Sample cell: diameter 10 mm, depth 2 mm
  Cumulation number of times: 1000 times
  Blocker: Used For example, according to the results of infrared spectropic measurement on the complex number 13 indicated in the later Example 2 and on a mere mixture of the carboxyalkylated polysaccharide number 2, which is its raw material and exemplified in Reference example 1, with the freeze-dried powder of the magnetic iron oxide aqueous sol indicated in Example 2, the peak (absorbance of the carbonyl group and hydroxyl group) positions near 1600 cm$^{-1}$ were 1600.7 cm$^{-1}$ and 1606.4 cm$^{-1}$, respectively. This difference is surmised to appear because the magnetic iron oxide particles and the polysaccharide carboxyalkyl ether are bound through at least part of the carboxyl groups in the complex of the invention.

Based on the above-mentioned several reasons, it is believed that the complex of the invention is a compound wherein the polysaccharide carboxyalkyl ether and the magnetic metal oxide are chemically bound.

About a diluted aqueous sol of the complex of the invention, translational diffusion coefficient was determined by the light scattering method and the diameter of the whole complex was determined by the equation of Stokes-Einstein. According to this, the diameter of complex of the invention is generally smaller than the diameter of the complex likewise synthesized using sodium hydroxide-treated modified dextran. For example, the diameters of the complexes of the complex numbers 3 and 7 shown in Example 1 are 72 and 73 nm, respectively, whereas the diameters of the complexes of the complex numbers 9 and 11 denoted in Reference example 4 are 124 and 117 nm, respectively. When it is taken into account that the diameter of the iron oxide part and the weight ratio of the polysaccharide to the iron are almost the same between the complex of the invention and the complex likewise synthesized using dextran, it can be said that the polysaccharide carboxymethyl ether molecule, a component of the complex of the invention does not take a spread structure in water but takes a structure such that it is rather unevenly distributed toward the magnetic iron oxide particles as a core substance. Namely, it is surmised that since the etherified substance molecule has many carboxyl groups in one molecule, it is bound to the magnetic iron oxide particles in many points in the formed complex.

The magnetism (for example, magnetization and coercive force) of the complex of the invention can be determined from the magnetization-magnetic field curve (so-called M-H curve) depicted using a vibrating sample magnet meter at room temperature. The magnetization in 1 tesla of the complex of the invention is about 1 to about 150 emu, preferably about 10 to about 150 emu per 1 g of the metal. Further, the coercive force of the complex of the invention increases in proportion as the size of the used magnetic metal oxide particles enlarges, and for example in the particle size of 20 nm or less the coercive force is about 20 oersteds or less and the complex is substantially superparamagnetic, while in the size of 100 nm or more the coercive force is about 50 to about 300 oersteds and the complex becomes ferromagnetic.

The T$_2$ relaxivity [unit: (sec.mM)$^{-1}$] of the complex of the invention in the form of aqueous sol can be determined by depicting the resonance curve of the proton of water on aqueous sols obtained by diluting the complex of the invention with water so as to give various concentrations and on the water used for the dilution using CW-NMR of 60 MHz (magnetic filed being about 1.4 teslas); determining the half-width $\Delta \nu_{\frac{1}{2}}$ (unit: Hz) of the obtained peak; calculating $1/T_2$ (unit: $\sec^{-1}$) $= \pi \cdot \Delta \nu_{\frac{1}{2}}$, plotting the relation of $1/T_2$ to the metal concentration (unit: mM) in the aqueous sol of the measurement sample, and determining the $T_2$ relaxivity from the inclination of the straight line determined by least square. The thus calculated $T_2$ relaxivity of the complex in the form of aqueous sol of the invention is generally about 5 $(\sec \cdot mM)^{-1}$ to about 1,000 $(\sec \cdot mM)^{-1}$.

The complex of the invention in the form of aqueous sol has an advantage that it has an extremely high stability in preservation. Namely, in the stability-in-preservation test wherein the complex aqueous sol of the invention is preserved at 55° to 80° C. and external changes such as the presence of precipitate and observed over the lapse of time, in proportion as the molecular weight and substitution degree of the polysaccharide carboxyalkyl ether used in the synthesis of the complex of the invention increase, the term before the external changes being observed lengthens and the stability of the complex increases. For example, when, as shown in the later Test example 1 the complex aqueous sol having an iron concentration of 25 mg/ml is placed in a glass ampoule, preserved at 80° C. and its external changes are observed over the lapse of time, no external change is observed for one month or more to six months or more, whereas when the complex aqueous sol synthesized using NaOH-treated modified dextran is preserved under the same conditions, the deposition of precipitate or gelation is observed 3 to 10 days later. Similar tendency is observed in an autoclave at 110° to 130° C. (sterilization with heating).

According to intravenous administration using mice, the acute toxicity $LD_{50}$ of the complex of the invention in the form of aqueous sol is about 40 to about 80 mmol/kg in terms of the metal, and low toxic compared to the complex obtained using dextran or sodium hydroxide-modified dextran. Namely, as shown in the later Test example 2, the $LD_{50}$ of the complex of the invention in a preferred embodiment, for example the complex of the complex number 4 obtained in Example 1 was 120 mmol(Fe)/kg. It can be said in general that complexes in preferred embodiments of the present invention are low toxic about 1.5 to about 3 times over complexes likewise synthesized using sodium hydroxide-modified dextran, in view of $LD_{50}$.

It was found that at least the magnetic particle part of the complex of the complex aqueous sol of the invention easily and promptly accumulates, after intravenous administration, in internal organs where the reticuloendothelial system develops such as liver, spleen and bone marrow, and particularly in a low dose (for example, 0.1 mmol/kg or less as the metal) most of, probably substantially all the administered complex accumulates in the Kupffer star cells in the liver. Based on this fact, the metabolism of these complexes was evaluated by measuring the degree of the magnetization of the liver using CW-NMR.

Namely, a complex aqueous sol is intravenously administered to mice in an amount of 0.1 mmol/kg as the metal; $1/T_2$ ($\sec^{-1}$) is determined in the same manner as in the measurement of $T_2$ relaxivity on the mouse liver at the point of time when the time of 1 hour, 2 hours, 4 hours, 1 day, 3 days, 7 days and 14 days elapsed after the administration; correction is made using the $1/T_2$ value of the liver of the non-administered mice group; and then the metabolism of each complex is calculated as half life from the relation with time after the administration. The half life of the complex of the complex number 7 shown in a preferred embodiment, e.g. Example 1 of the invention is about 2.7 days, while that of the complex of the complex number 11 likewise synthesized and denoted in Reference example 4 is about 5.4 days, and thus it is seen that the complex of the invention is more easily metabolized.

Complexes capable of becoming aqueous sol among the complexes of the invention prepared using as magnetic particles magnetic metal oxide particles having a diameter of about 2 to about 100 nm, preferably about 5 to about 15 nm can be used as a so-called magnetic fluid in industrial fields such as mechanical seal materials, magnetic clutches and magnetic inks, and preferably can safely be used in the biological field and the medical field, for example as an iron-supplementing agent, an X-ray contrast medium, a MRI contrast medium, or a carrier in the measurement of bloodstream of further in the concentrated administration of a drug to a topical part utilizing magnetic field and/or the recovery or removal of a living body-derived substance, or the like. The complexes of the invention wherein the diameter of the magnetic metal oxide particles as a starting raw material is about 100 nm or more can advantageously be used in the biological field and the medical field, for example as an X-ray contrast medium, a carrier in the recovery or removal of a living body-derived substance, or the like.

In the complexes of the invention preferably usable as a MRI contrast medium, the limiting viscosity of the polysaccharide carboxyalkyl ether is in the range of preferably about 0.02 to about 0.5 dl/g, more preferably about 0.05 to about 0.3 dl/g; used as the polysaccharide is preferably dextran, starch, cellulose or pullulan; used as the carboxyalkyl ether is preferably carboxymethyl ether, carboxyethyl ether or carboxypropyl ether, more preferably carboxymethyl ether; and the substitution degree of the polysaccharide carboxyalkyl ether is preferably in the range of about 0.1 to about 0.5 mol/MSU. On the other hand, as for the magnetic metal oxide particles, a magnetic iron oxide or ferrite is preferred and a magnetic iron oxide is more preferred, and it is preferred that the diameter of the magnetic particles is in the range of about 5 to about 15 nm and the $T_2$ relaxivity is generally in the range of about 20 to about 300 $(\sec \cdot mM)^{-1}$.

When the complex of the invention is used as a MRI contrast medium, it is desirable to use the complex in the form of aqueous sol. Although the concentration of the complex can be varied over a wide range, usually it is suitable that the concentration is in the range of about 0.1 to about 2 mol/l in terms of the metal. Further, in the preparation of the aqueous sol, it is also possible to add various physiologically acceptable auxiliaries, for example an inorganic salt such as sodium chloride, a monosaccharide such as glucose, a sugar alcohol such as mannitol or sorbitol, an organic acid salt such as a citrate or a tartrate, a phosphate buffer agent or Tris buffer agent. When the complex of the invention is used as a MRI contrast medium, the use amount varies depending on diagnostic sites but is in the range of usually about 1 μmol/kg to 10 mmol/kg, preferably about 2 μmol/kg to 1 mmol/kg in terms of the metal. As methods of administration, there can, for example, be artery, the bladder or the like, and in some case oral administration or direct administration into the intestine is also possible. For example when the complex in a preferred embodiment of the invention is intravenously administered, many of its molecules gather in the reticuloendothelial system, particularly in the liver relatively swiftly, for example within several hour, and as a result the MRI photographing of the liver is appropriately made. When there is a lesion part where the reticuloendothelial system function is lowered for example a cancer in the liver, the complex molecules of the invention does not gather at all or only partly gather at the lesion part compared to other normal sites, and therefore the identification of the lesion part can easily be made by MRI photographing. The complex of the invention has an effect as a contrast medium on a $T_1$ image as well as a $T_2$ image.

BRIEF DESCRIPTION OF THE DRAWINGS

FIG. 1, FIG. 2 and FIG. 3 are X-ray diffraction patterns of the complex of the number 7 indicated in Example 1, the complex of the number 15 indicated in Example 2 and the complex of the number 24 indicated in Example 4, respectively.

FIG. 4 is the infrared absorption spectrum of the complex of the number 13 denoted in Example 2 and FIG. 5 is the infrared absorption spectrum when the carboxyalkylated polysaccharide powder of the number 2 denoted in Reference example 1 was admixed with the freeze-dried powder of the magnetic iron oxide aqueous sol used in Example 2 so that the composition of the mixture became the same with that of the complex of the number 13.

BEST MODE FOR CARRYING OUT THE INVENTION

Figure 1:
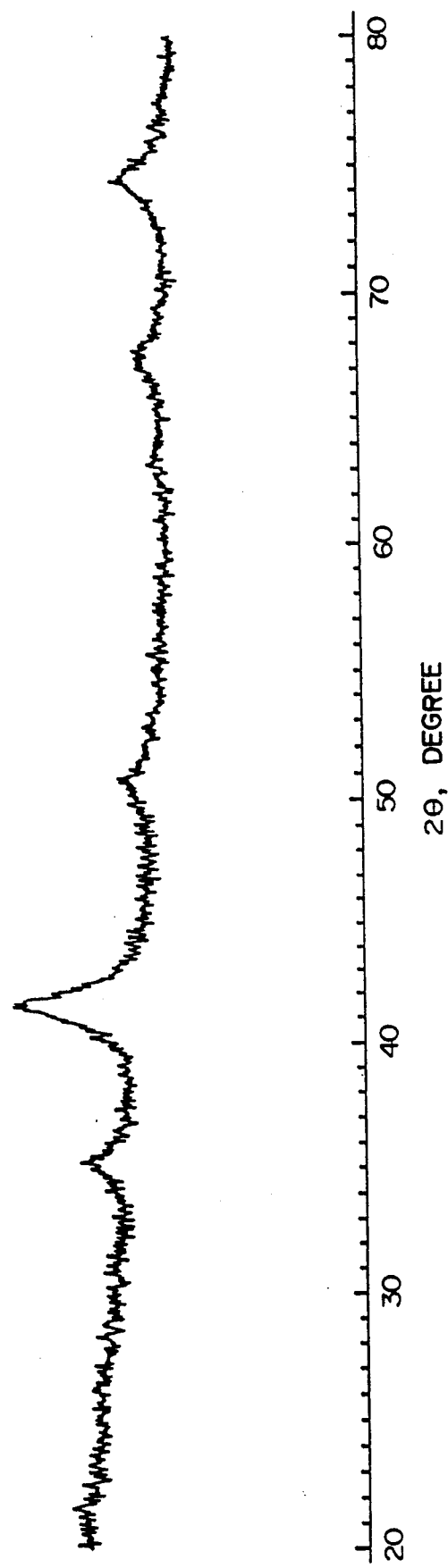
FIG. 1, FIG. 2 and FIG. 3 are the X-ray diffraction patterns of the complexes of the invention obtained using a powder X-ray diffractometer (target: Co, wavelength: 1.790 Å)
Figure 2:
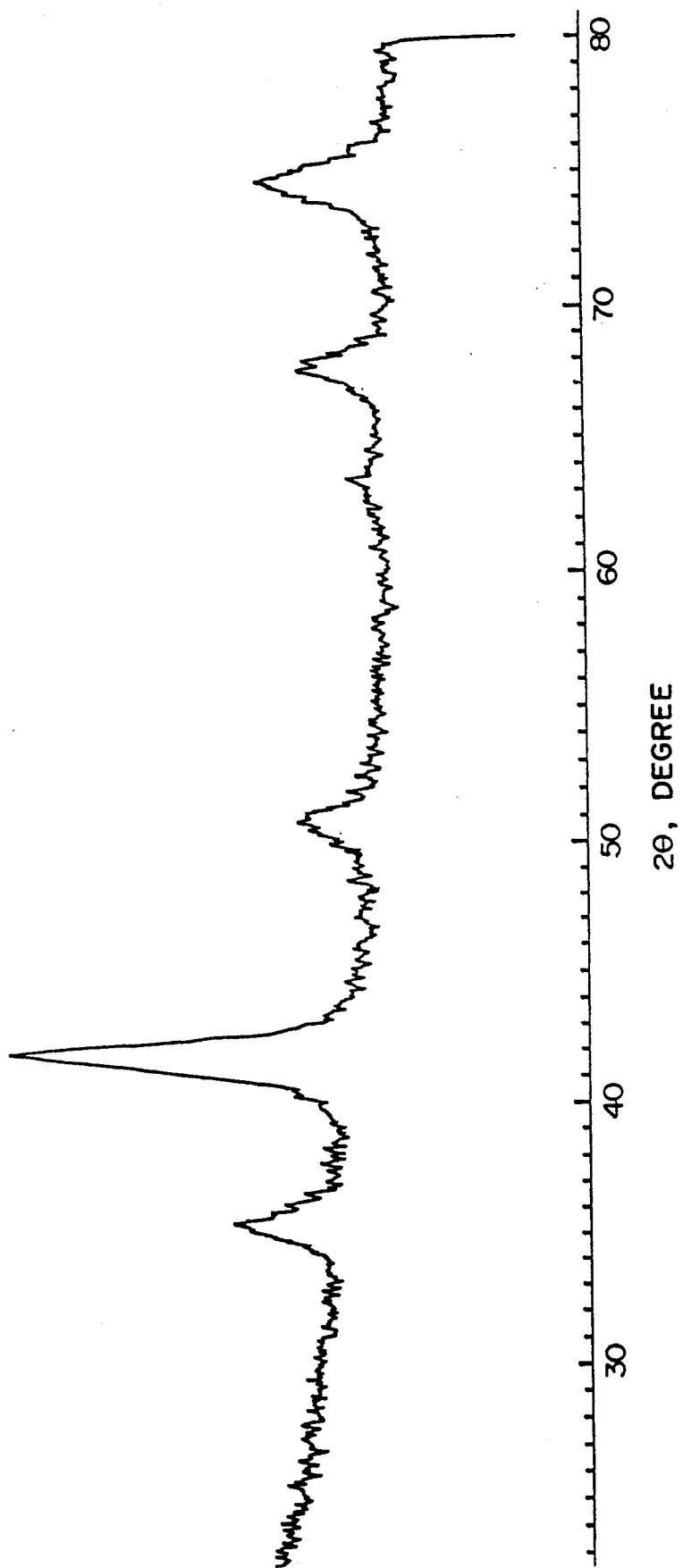
Figure 3:
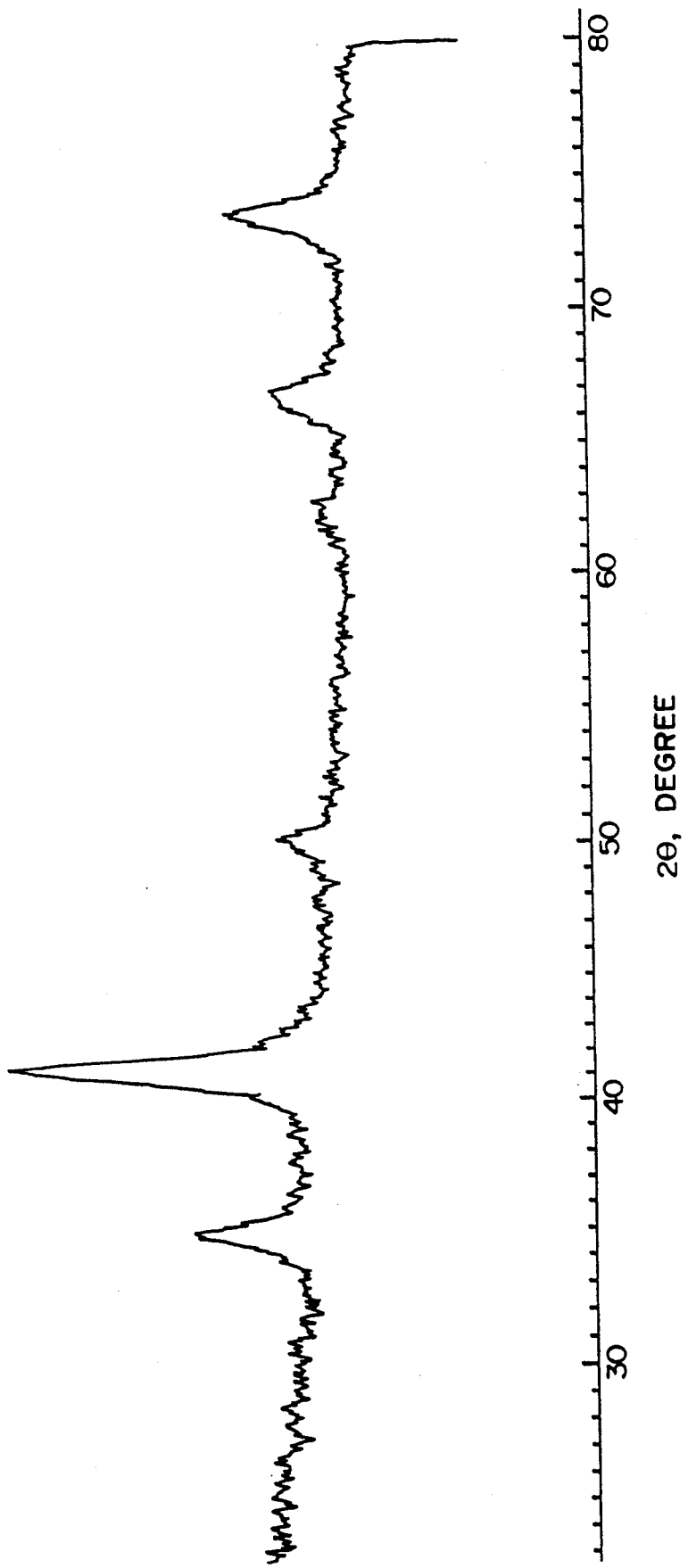
Figure 4:
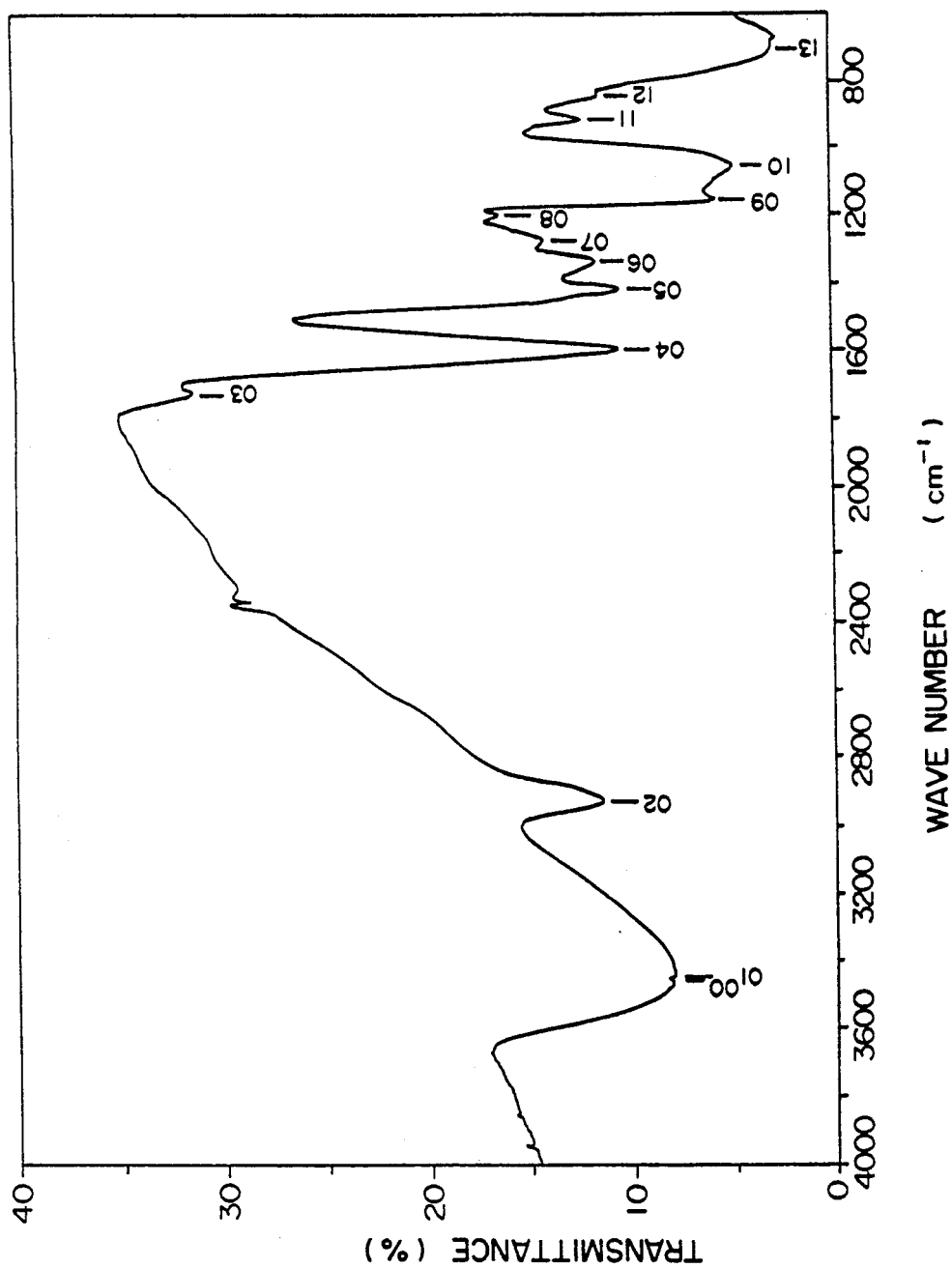
FIG. 4 and FIG. 5 are infrared absorption spectra of the powder samples obtained by the diffuse reflectance method using a FT-infrared spectrometer.
Figure 5:
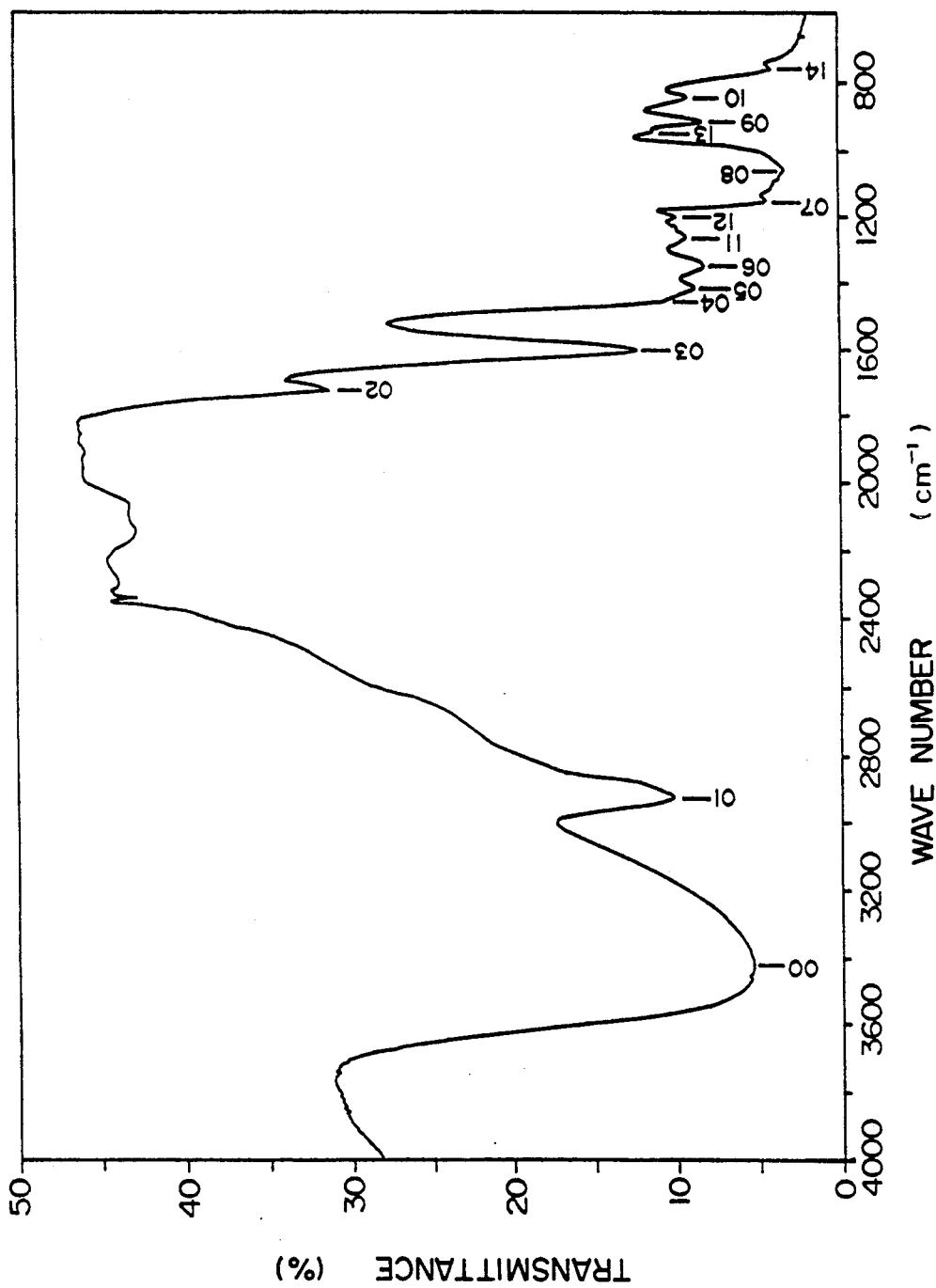

This invention is further specifically described below by reference examples, examples and test examples.

REFERENCE EXAMPLE 1

Preparation of various polysaccharide carboxymethyl ethers 300 g portions of the various polysaccharides are respectively dissolved in 700 ml portions of water, 10 and an aqueous sodium hydroxide (NaOH) solution and monochloroacetic acid ($ClCH_2COOH$) are added to each solution at 20° C. or less, followed by stirring at 60° C. for 2 hours. After being cooled, each solution is adjusted to pH 8 with hydrochlonic acid, and then 1.0 to 2.5 times as much methanol as the reaction solution volume is added in accordance with the intrinsic viscosity of the used polysaccharide and the substitution degree of the carboxymethyl groups (hereinafter referred to (CM groups). The deposit is redissolved in 1 l of water, the operation to obtain a deposit by adding methanol is repeated further three times, the resulting deposit is dissolved in 1.2 l of water, the solution is adjusted to pH 8 with an aqueous sodium hydroxide solution and filtered with a glass filter, and the filtrate is concentrated under reduced pressure and freeze dried to obtained a sodium salt of the polysaccharide carboxymethyl ether. In Table 1 are shown the kind of the used polysaccharides, the used amounts of sodium hydroxide and monochloroacetic acid, and the yield and properties of the resulting polysaccharide carboxymethyl ethers (hereinafter referred to as CM-lated (carboxymethylated) polysaccharides).

TABLE 1

| No. of CA-lated poly-saccharide[1] | Synthesis of CM-lated polysaccharide | | | | Properties of CM-lated polysaccharide | |
|---|---|---|---|---|---|---|
| | Kind of poly-saccharide | NaOH (g)[2] | $ClCH_2COOH$ (g) | Yield of CM-lated polysaccharide (g) | CM group substitution degree mol/MSU[3] | $[\eta]^{4)}$ dl/g |
| 1 | Reduced dextran | 51.9 | 61.3 | 233 | 0.10 | 0.0558 |
| 2 | Same as above | 103.7 | 122.5 | 262 | 0.30 | 0.0488 |
| 3 | Same as above | 103.7 | 122.5 | 287 | 0.25 | 0.0705 |
| 4 | Same as above | 57.7 | 67.4 | 280 | 0.11 | 0.0907 |
| 5 | Same as above | 114.1 | 134.8 | 305 | 0.29 | 0.0910 |
| 6 | Same as above | 25.9 | 30.6 | 283 | 0.05 | 0.111 |
| 7 | Same as above | 51.9 | 61.3 | 294 | 0.14 | 0.114 |
| 8 | Same as above | 103.7 | 122.5 | 306 | 0.26 | 0.115 |
| 9 | Same as above | 178.0 | 211.0 | 328 | 0.48 | 0.122 |
| 10 | Dextran | 103.7 | 122.5 | 302 | 0.27 | 0.106 |
| 11 | Same as above | 428.0 | 508.0 | 413 | 1.10 | 0.131 |
| 12 | Same as above | 103.7 | 122.5 | 310 | 0.26 | 0.211 |
| 13 | Amylose | 103.7 | 122.5 | 311 | 0.25 | 0.357 |
| 14 | Pullulan | 103.7 | 122.5 | 315 | 0.23 | 0.319 |

[1)]Number of carboxyalkyl ether of a polysaccharide
[2)]Each is used after being dissolved in 300 ml of water
[3)]Substitution degree of carboxymethyl ether groups per monosaccharide unit; MSU means monosaccharide unit.
[4)]Intrinsic viscosity in 1 M NaCl of 25° C.

REFERENCE EXAMPLE 2

Lowering the molecular weight of carboxymethylcellulose 100 g of sodium salt of carboxymethylcellulose on the market (substitution degree: 0.67 mol/MSU) is dissolved in 2 l of water, 60 ml of 5N NaOH and 134 ml of % $H_2O_2$ are alternately added over a period of 1 hour while the solution is maintained at 30° C. under stirring, and the mixture is stirred for further 2 hours. The reaction solution is adjusted to pH about 8 with hydrochloric acid and concentrated under reduced pressure to make the reaction solution amount 1 l, and then 2 l of acetone is added thereto. The deposited precipitate is dissolved in 600 ml of water, and the operation to obtain a precipitate by adding 1.2 l of acetone is repeated three times. The aqueous solution of the resulting precipitate is adjusted to pH 8 and filtered with a glass filter, and the filtrate is concentrated under reduced pressure and freeze dried to obtain powder of sodium salt of carboxymethylcellulose whose molecular weight is lowerd (CA-lated polysaccharide number 15). Yield 54 g. CM group substitution degree=0.55 mol/MSU, $[\eta]=0.319$ dl/g.

REFERENCE EXAMPLE 3

Preparation of carboxyethyl ether of dextran 300 g of dextran having an intrinsic viscosity $[\eta]$ of 0.10 is dissolved in 700 ml of water, a solution obtained by dissolving 128 g of sodium hydroxide in 300 ml of water, and 174 g of 3-chloropropionic acid are added thereto with stirring at 20° C. or less, followed by reaction at 60° C. for 4 hours. Thereafter, the reaction solution is treated in the same manner as in Reference example 1 to obtain the powder of sodium salt of dextran carboxyethyl ether (CA-lated polysaccharide number 16). Yield 301 g, carboxyethyl group substitution degree =0.25 mol/MSU, ) $[\eta]=0.117$ dl/g.

EXAMPLE 1

86 g portions of the various CM-lated polysaccharide sodium salts prepared in Reference example 1 are dissolved in 240 ml portions of water, respectively. A solution obtained by dissolving 45.4 g of ferric chloride hexahydrate and 21.6 g of ferrous chloride tetrahydrate in 160 ml of water in a nitrogen stream is added to each solution, and a 3N aqueous sodium hydroxide solution is added under stirring to pH 11 with heating. Then, after the pH is adjusted to 7.0 with the addition of hydrochloric acid, the mixture is refluxed with heating for 1 hour. After being cooled, the mixture is centrifuged, methanol is added to the supernatant until the concentration becomes 42 to 48% to precipitate a complex, the precipitate is dissolved in water, and the solution is dialyzed against running water for 16 hours. The dialyzed solution is adjusted to pH 8.0 with sodium hydroxide, concentrated under reduced pressure and filtered with a membrane filter (pore size: 0.45 μm), and the filtrate is freeze dried. The yield and properties of the obtained various complexes are shown in Table 2.

REFERENCE EXAMPLE 4

86 g portions of modified dextrans obtained by treating dextrans having various intrinsic viscosity with sodium hydroxide are dissolved in 240 ml portions of water, respectively, followed by the same operation as in Example 1. The yield and properties of the resulting complexes are shown in Table 3.

TABLE 3

| | | | Properties of complex | | | | |
|---|---|---|---|---|---|---|---|
| Complex No. | Dextran $[\eta]^{1)}$ (dl/g) | Yield (g) | Iron content (w %) | Dextran content (w %) | Particle diameter of the iron oxide part (nm) | Magnetization in 10,000 oersted (emu/g-Fe) | $T_2$ relaxivity (sec · mM)$^{-1}$ |
| 8 | 0.0492 | 26.2 | 42 | 36 | 8.7 | 98 | 260 |
| 9 | 0.0695 | 37.4 | 34 | 56 | 6.0 | 82 | 240 |
| 10 | 0.0905 | 42.1 | 32 | 58 | 6.1 | 86 | 220 |
| 11 | 0.107 | 38.0 | 31 | 60 | 7.2 | 85 | 249 |

$^{1)}$Intrinsic viscosity of modified dextran in 1 M NaCl of 25° C.

EXAMPLE 2

To a slurry obtained by adding 1.75 l of water to 3 l of Amberlite ® IRA-410 (an ion exchange resin produced by Rohm and Haas Company) is added with stirring at about 20° C. a mixed solution of 600 ml of a 1M aqueous ferric chloride solution with 300 ml of a 1M aqueous ferrous chloride solution while the pH of the resulting mixture is maintained at 8 to 8.7. The mixture is adjusted to pH 1.6 with the addition of concentrated hydrochloric acid and stirred at the same pH for 1 hour. After the resin is removed by filtration, the filtrate is ultrafiltered up to pH 2.5 while water is added, whereby 1.15 l of a magnetic iron oxide aqueous sol (iron concentration: 30.2 mg/ml, particle size: 8.0 nm) is obtained. 330 ml portions of this sol (10 g as iron) are mixed respectively with solutions obtained by dissolving 45 g portions of the various CA-lated polysaccharide sodium salts prepared in Reference examples 1, 2 and 3 respectively in 225 ml portions of water. Each mixture is refluxed with heating for 1 hour. After being cooled, each reaction mixture is centrifuged, methanol is added to the supernatant up to 42 to 48% concentration, the resulting precipitate is dissolved in water, and the solution is dialyzed against flowing water for 16 hours. The dialyzed solution is adjusted to pH 7.5 and if necessary concentrated under reduced pressure. The solution is filtered with a glass filter and freeze dried.

The yield and properties of the obtained various complexes are shown in Table 4.

TABLE 2

| | | | Properties of complex | | | | |
|---|---|---|---|---|---|---|---|
| Complex No. | No. of used CA-lated polysaccharide | Yield (g) | Iron content (w %) | Content of CM-lated polysaccharide (w %) | Particle size of the iron oxide part (nm) | Magnetization in 10,000 oersted (emu/g-Fe) | $T_2$ relaxivity (sec · mM)$^{-1}$ |
| 1 | 1 | 31.4 | 42 | 36 | 8.5 | 64 | 220 |
| 2 | 2 | 39.6 | 36 | 44 | 10.1 | 59 | 180 |
| 3 | 3 | 43.1 | 32 | 54 | 8.4 | 61 | 180 |
| 4 | 4 | 43.6 | 32 | 53 | 7.5 | 85 | 190 |
| 5 | 5 | 42.6 | 32 | 54 | 6.7 | 89 | 140 |
| 6 | 7 | 41.5 | 34 | 44 | 7.5 | 80 | 180 |
| 7 | 8 | 49.3 | 28 | 59 | 7.3 | 85 | 130 |

TABLE 4

| Complex No. | No. of the used CA-lated polysaccharide | Yield (g) | Properties of complex ||||||
|---|---|---|---|---|---|---|---|
| | | | Iron content (w %) | CA-lated polysaccharide content (w %) | Particle size of the iron oxide part (nm) | Magnetization in 10,000 oersted (emu/g-Fe) | $T_2$ relaxivity $(sec \cdot mM)^{-1}$ |
| 12 | 1 | 19.2 | 48 | 31 | 7.9 | 89 | 280 |
| 13 | 2 | 20.9 | 45 | 34 | 8.1 | 91 | 270 |
| 14 | 6 | 23.2 | 41 | 39 | 8.0 | 91 | 280 |
| 15 | 7 | 23.4 | 41 | 40 | 8.2 | 92 | 290 |
| 16 | 10 | 19.1 | 47 | 34 | 7.7 | 92 | 290 |
| 17 | 11 | 5.5 | 51 | 28 | 8.0 | 90 | 280 |
| 18 | 12 | 15.2 | 42 | 42 | 7.9 | 91 | 300 |
| 19 | 13 | 15.3 | 40 | 44 | 7.8 | 92 | 280 |
| 20 | 14 | 15.5 | 41 | 43 | 7.9 | 91 | 290 |
| 21 | 15 | 15.2 | 25 | 62 | 8.0 | 91 | 270 |
| 22 | 16 | 20.2 | 45 | 36 | 8.1 | 92 | 280 |

EXAMPLE 3

43 g of the CM-lated polysaccharide sodium salt of the number 9 is dissolved in 120 ml of water, 140 ml of a 3 N aqueous sodium hydroxide solution is added thereto, and while this solution is warmed, a solution obtained by dissolving 22.7 g of ferric chloride hexahydrate and 10.8 g of ferrous chloride tetrahydrate in a nitrogen stream is added thereto with stirring. The mixture is adjusted to pH 7.0 with hydrochloric acid and refluxed with heating for 1 hour, and then the same operation as in Example 2 is made. Yield 3.4 g. The properties of the resulting complex are denoted in Table 5.

TABLE 5

| Complex No. | Iron content (w %) | CM-lated polysaccharide content (w %) | Particle size of the iron oxide part (nm) | Magnetization in 10,000 oersted (emu/g-Fe) | $T_2$ relaxivity $(sec \cdot mM)^{-1}$ |
|---|---|---|---|---|---|
| 23 | 32 | 52 | 8.4 | 87 | 130 |

EXAMPLE 4

Zinc ferrite complex

To a mixed solution of 50 ml of 1M zinc sulfate (ZnSO₄) and 150 ml of 0.5M ferric sulfate [Fe₂(SO₄)₃] (Zn/Fe ratio=⅓) is dropwise added with stirring and warming 210 ml of a 3N aqueous sodium hydroxide solution, followed by reflux with heating for 3 hours. After being cooled, the reaction mixture is centrifuged, and the operation to wash the precipitate with 450 ml of water is repeated 4 times in total. About 2.5 ml of concentrated hydrochloric acid is added to the obtained ferrite suspension (liquid volume 300 ml) to make the pH 1.7, followed by stirring for 16 hours. To 300 ml of the obtained ferrite aqueous sol (pH 2.1) is added a solution obtained by dissolving 45 g of the CM-lated polysaccharide of the number 8 denoted in Reference example 1 in 90 ml of water, and the mixture is adjusted to pH of about 7 with sodium hydroxide and refluxed with heating for 1 hour. After the reaction solution is cooled, methanol is added thereto up to 45% concentration, the deposited precipitate is dissolved in 150 ml of water, the solution is centrifuged at 3,000 rpm for 30 minutes, and an aqueous sol of the complex obtained by removing the precipitate is dialyzed against flowing water for 16 hours using a cellophane tube. The dialyzed aqueous sol is adjusted to pH 8.0 with sodium hydroxide and filtered with a glass filter (G3), and the filtrate is concentrated under reduced pressure and freeze dried. Yield 27 g. The properties of the obtained complex are denoted in Table 6.

TABLE 6

| Complex No. | Iron content (w %) | Zinc content (w %) | CM-lated polysaccharide content (w %) | Particle size of the ferrite part (nm) | Magnetization in 10,000 oersted (emu/g-Fe) | $T_2$ relaxivity $(sec \cdot mM)^{-1}$ |
|---|---|---|---|---|---|---|
| 24 | 26 | 9.8 | 48 | 10.3 | 27 | 22 |

TEST EXAMPLE 1

Stability test

The complexes prepared in Example 1 and Reference Example 4 were dissolved in water to prepare aqueous sols each having an iron content of 25 mg/ml, the aqueous sols were filtered with a membrane filter of 0.45 μm and the filtrates were charged into 5 ml ampoules. These ampoules were preserved at 80°±2° C. and examined with the naked eye over the lapse of time for the change (gelation or the deposition of a precipitate) of the complex sols. The results of this preservation test are shown in Table 7.

TABLE 27

| Complex No. | Result | Complex No. | Result |
|---|---|---|---|
| 1 | A precipitate started to deposit in 2 weeks | 7 | Stable for 3 months or more |
| 2 | A precipitate started to deposit in 1 month | 8 | Gelatin in 4 days |
| 3 | Stable for 3 months or more | 9 | Gelation in 1 week |
| 4 | A precipitate started to deposit in 2 months | 10 | Gelation in 1 week |
| 5 | Stable for 3 months or more | 11 | Gelation in 1 week |
| 6 | A precipitate deposited in | | |

TABLE 27-continued

| Complex No. | Result | Complex No. | Result |
|---|---|---|---|
| | 1 month; gelation in 2.5 months | | |

TEST EXAMPLE 2

Safety test

The acute toxicity ($LD_{50}$) of each complex prepared in Example 1 or Reference example 4 was determined. An aqueous sol of each complex was intravenously administered to male dd strain mice (5 weeks old) of groups, each consisting of 3 to 10 mice in amounts of 10, 20, 40, 80 and 160 mmol/kg as iron, respectively, the animals were observed for 1 week for life or death, and $LD_{50}$ was calculated by the Litchfield & Wilcoxon method. The $LD_{50}$ values of the respective complexes are shown in Table 8.

TABLE 8

| Complex No. | $LD_{50}$ (mmol(Fe)/kg) | Complex No. | $LD_{50}$ (mmol(Fe)/kg) |
|---|---|---|---|
| 1 | 46 | 7 | 92 |
| 2 | 87 | 8 | 30 |
| 3 | 120 | 9 | 30 |
| 4 | 120 | 10 | 45 |
| 5 | 87 | 11 | 28 |
| 6 | 120 | | |

Industrial Applicability

The complex of this invention is extremely excellent in stability in preservation in the form of aqueous sol, has only a low toxicity and is useful particularly in medical use, for example as a nuclear magnetic resonance imaging (MRI) control agent, a topically drug-administering carrier, an iron-supplementing agent, an X-ray control agent or the like, and further can also be used as a magnetic fluid in industrial fields, for example the mechanical seal material, magnetic clutch and magnetic ink fields.

What we claim is:

1. A complex of a carboxyalkyl ether of a polysaccharide having an intrinsic viscosity of about 0.02 to about 0.05 dl/g at 25° C. with a magnetic metal oxide.

2. The complex of claim 1 wherein the polysaccharide is a neutral polysaccharide.

3. The complex of claim 2 wherein the polysaccharide is selected from the group consisting of dextran, starch, cellulose and pullulan.

4. The complex of claim 1 wherein the carboxyalkyl ether is at least one selected from a carboxymethyl ether, a carboxyethyl ether and a carboxypropyl ether.

5. The complex of claim 1 wherein the carboxyalkyl ether of the polysaccharide has an intrinsic viscosity in the range of about 0.05 to about 0.3 dl/g at 25° C.

6. The complex of claim 1 wherein the carboxyalkyl ether of the polysaccharide has a substitution degree in the range of about 0.05 to about 1.0 mol/MSU.

7. The complex of claim 1 wherein the magnetic metal oxide is represented by the formula $$(M^{II}O)_l \cdot M_2^{III}O_3$$

wherein $M^{II}$ denotes a divalent metal atom, $M^{III}$ denotes a trivalent metal atom and l is a real number in the range of $0 \leq l \leq 1$.

8. The complex of claim 7 wherein the magnetic metal oxide is a ferrite represented by the formula $$(M^{II}O)m \cdot Fe_2O_3$$

wherein $M^{II}$ denotes a divalent metal atom and m is a real number of $0 \leq m \leq 1$.

9. The complex of claim 8 wherein the magnetic metal oxide is a magnetic iron oxide represented by the formula $$(FeO)n \cdot Fe_2O_3$$

wherein n is a real number in the range of $0 \leq n \leq 1$.

10. The complex of claim 9 wherein the magnetic iron oxide is γ-iron oxide or magnetite.

11. The complex of claim 1 wherein the magnetic metal oxide is represented by the formula $$M^{II}M^{IV}O_3 \text{ or } M^{IV}O_2$$

wherein $M^{II}$ represents a divalent metal atom and $M^{IV}$ represents a tetravalent metal atom.

12. The complex of claim 11 wherein the magnetic metal oxide is selected from $NiMnO_3$, $CoMnO_3$ and $CrO_2$.

13. The complex of claim 1 wherein the magnetic metal oxide has a particle size of about 2 to about 100 nm.

14. The complex of claim 1 wherein the magnetic metal oxide has a magnetization in the range of about 1 to about 150 emu per 1 g of the metal in a magnetic field of 1 tesla at 20° C.

15. The complex of claim 1 wherein the magnetic metal oxide has a magnetization in the range of about 10 to about 150 emu per 1 g of the metal in a magnetic fieled of 1 tesla at 20° C.

16. The complex of claim 1 wherein the carboxyalkyl ether of the polysaccharide is contained in an amount of 0.05 to 10 parts by weight per part by weight of the metal in the magnetic metal oxide.

17. The complex of claim 1 wherein the carboxyalkyl ether of the polysaccharide is contained in an amount of 0.2 to 5 parts by weight per 1 part by weight of the metal in the magnetic metal oxide.

18. The complex of claim 1 wherein the diameter thereof measured by the light scattering method is about 10 to about 500 nm.

19. A MRI molding agent comprising the complex of claim 1.

20. A process for preparing the complex of claim 1 which comprises:
   (a) reacting an aqueous sol or suspension containing particles of a magnetic metal oxide with the carboxyalkyl ether of a polysaccharide having an intrinsic viscosity of about 0.02 to about 0.5 dl/g and a substitution degree of about 0.05 to about 1.0 mol/MSU, or
   (b) carrying out the reaction by mixing a salt of a divalent metal, a salt of a trivalent metal and a base while stirring in an aqueous system in the presence of the carboxyalkyl ether of the polysaccharide having an intrinsic viscosity of about 0.02 to about 0.5 dl/g and a substitution degree of about 0.05 to about 0.5 mol/MSU.

* * * * *

UNITED STATES PATENT AND TRADEMARK OFFICE
CERTIFICATE OF CORRECTION

PATENT NO. : 5,204,457  
DATED : April 20, 1993  
INVENTOR(S) : Shigeo Maruno et al.

Page 1 of 1

It is certified that error appears in the above-identified patent and that said Letters Patent is hereby corrected as shown below:

Column 19, claim 1,
Line 3, change "0.05" to -- 0.5 --.

Signed and Sealed this

Eighth Day of January, 2002

*Attest:*

*Attesting Officer*

JAMES E. ROGAN
*Director of the United States Patent and Trademark Office*